(12) United States Patent
Cohen et al.

(10) Patent No.: US 6,488,933 B2
(45) Date of Patent: *Dec. 3, 2002

(54) PREPARATIONS FOR THE TREATMENT OF T CELL MEDIATED DISEASES

(75) Inventors: Irun R. Cohen, Rehovot (IL); Dana Elias, Rehovot (IL); Meir Shinitzky, Kfar Shmaryahu (IL)

(73) Assignee: Yeda Research and Development Co. Ltd., Rehovot (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 08/981,861

(22) PCT Filed: Jul. 2, 1996

(86) PCT No.: PCT/US96/11373
§ 371 (c)(1),
(2), (4) Date: Apr. 14, 1998

(87) PCT Pub. No.: WO97/02016
PCT Pub. Date: Jan. 23, 1997

(65) Prior Publication Data
US 2002/0086030 A1 Jul. 4, 2002

(30) Foreign Application Priority Data
Jul. 5, 1995 (IL) .................................... 114458

(51) Int. Cl.$^7$ ............................................ A61K 39/00
(52) U.S. Cl. ................ 424/185.1; 424/184.1; 424/248.1; 424/283.1; 424/288.1; 514/13
(58) Field of Search .................... 424/184.1, 185.1, 424/248.1, 288.1, 283.1; 514/13

(56) References Cited

U.S. PATENT DOCUMENTS

| | | | |
|---|---|---|---|
| 3,169,094 A | | 2/1965 | Wretlind |
| 4,073,943 A | | 2/1978 | Wretlind et al. |
| 4,168,308 A | | 9/1979 | Wretlind et al. |
| 4,395,394 A | | 7/1983 | Wolff, III et al. |
| 4,474,773 A | | 10/1984 | Shinitzky et al. |
| 4,551,449 A | * | 11/1985 | Ladisch |
| 5,780,034 A | * | 3/1990 | Cohen et al. |
| 5,114,844 A | | 5/1992 | Cohen et al. |
| 5,254,339 A | | 10/1993 | Morein |
| 5,961,970 A | | 10/1999 | Lowell et al. |
| 5,998,366 A | | 12/1999 | Tobin et al. |

FOREIGN PATENT DOCUMENTS

| | | |
|---|---|---|
| EP | 359783 | 2/1990 |
| WO | WO 90/10449 | 9/1990 |
| WO | WO 90/14837 | 12/1990 |
| WO | WO91/08760 | 6/1991 |
| WO | WO91/12816 | 9/1991 |
| WO | WO 91/15225 | 10/1991 |
| WO | WO92/06704 | 4/1992 |
| WO | WO 95/11700 | 5/1996 |
| WO | WO96/19236 | 6/1996 |
| WO | WO97/01959 | 1/1997 |

OTHER PUBLICATIONS

Tisch et al. Cell 85:291–297, 1996.*
The Merck Manual p. 1106, 1992.*
Elias et al. Lancet 343:704–706, 1994.*
The Merck Manual. Berkow, ed., 16th ed. pp. 1106–1111, 1992.*
Tisch et al. PNAS 91:437, 1994.*
Ladisch et al. Clin. Immunol. & Immunopathology 25: 196 1982.*
Wabel, C. "Influence of Lecithin on Structure and Stability of Parenteral Fat Emulsions", Doctoral Thesis, Chapter 1, pp. 1–24 (1998).
Allegretta, Mark et al., "T cells responsive to myelin basic protein in patients with multiple schlerosis." Science, vol. 247, pp. 718–721 (1990).
Kohei, Ota et al., "T–cell recognition of an immuno–dominant myelin basic protein epitope in multiple sclerosis.", Letters to Nature, vol. 346, pp. 183–187 (1990).
Zamvil, Scott et al., "The T lymphocyte in experimental allergic encephalomyelitis.", Annu. Rev. Immunol., vol. 8, pp. 579–621 (1990).
Urban et al., "Autoimmune T cells: immune recognition of normal and variant peptide epitopes and peptide–based therapy.", Cell, vol. 59, pp. 257–271 (Oct. 20, 1989).
Martin et al., "Expiremental immunotherapies for multiple sclerosis", Springer Semin. Immunopathol., vol. 18, pp. 1–24 (1996).
Elias et al., "Vaccination against autoimmune mouse diabetes with a t–cell epitope of the human 65–kda heat shock protein", Proc. Natl. Sci. Acad. USA, vol. 88, pp. 3088–3091 (Apr. 1991).
Wraith et al., "A role for major histocompatibility complex binding peptides in the immunotherapy of autoimmune disease", Springer Semin. Immunopathol., vol. 14, pp. 95–101 (1992).

* cited by examiner

Primary Examiner—Patrick J. Nolan
Assistant Examiner—Gerald R. Ewoldt
(74) Attorney, Agent, or Firm—Winston & Strawn

(57) ABSTRACT

Metabolizable lipid emulsions, such as Intralipid and Lipofundin, are excellent vehicles for peptide therapy of autoimmune diseases and of other TH1 T cell mediated diseases or conditions, as it promotes a TH1 to TH2 cytokine shift. Such emulsions may be used in conjunction with an antigen recognized by inflammatory T cells associated with the pathogenesis of a T cell mediated disease or condition for the therapeutic treatment of such

7 Claims, 6 Drawing Sheets

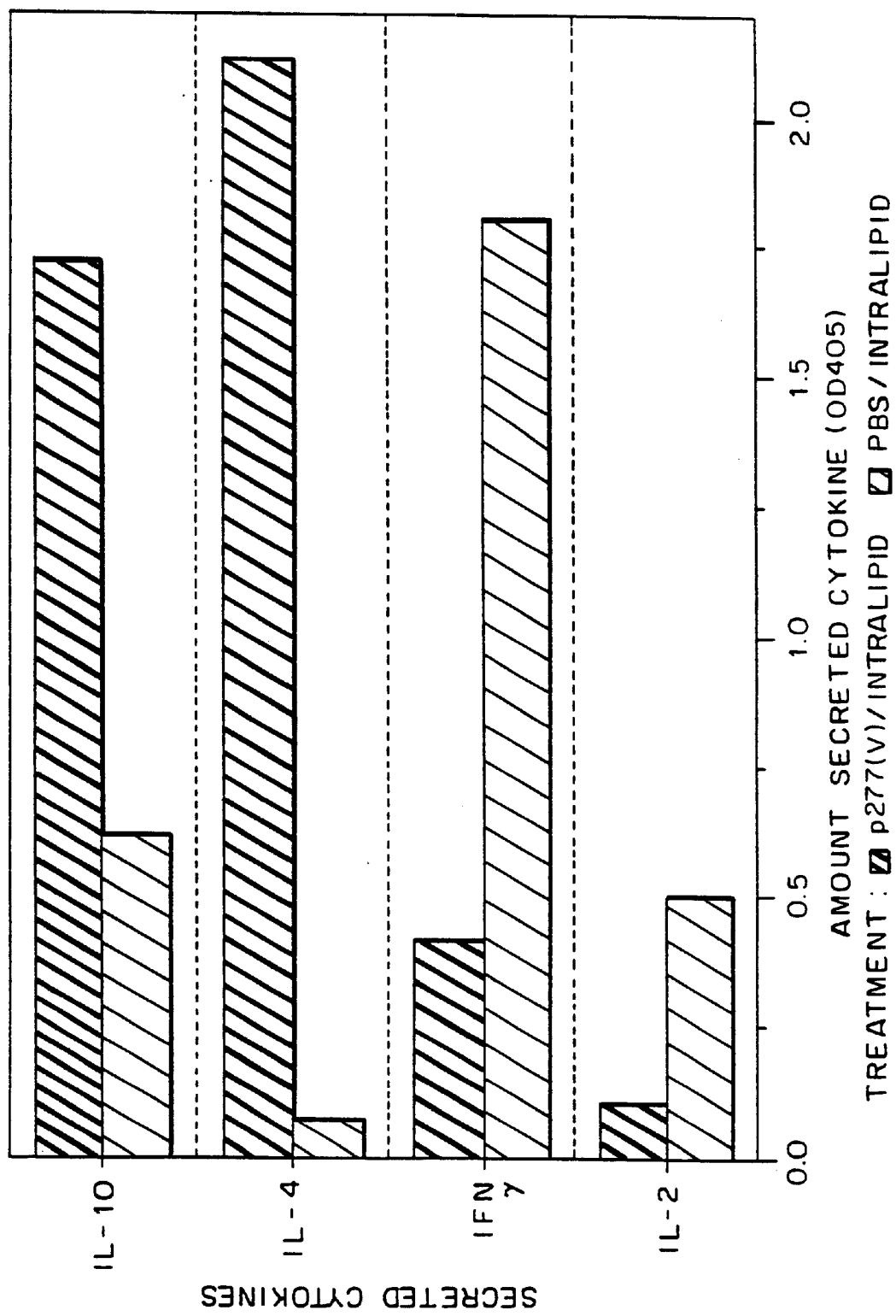

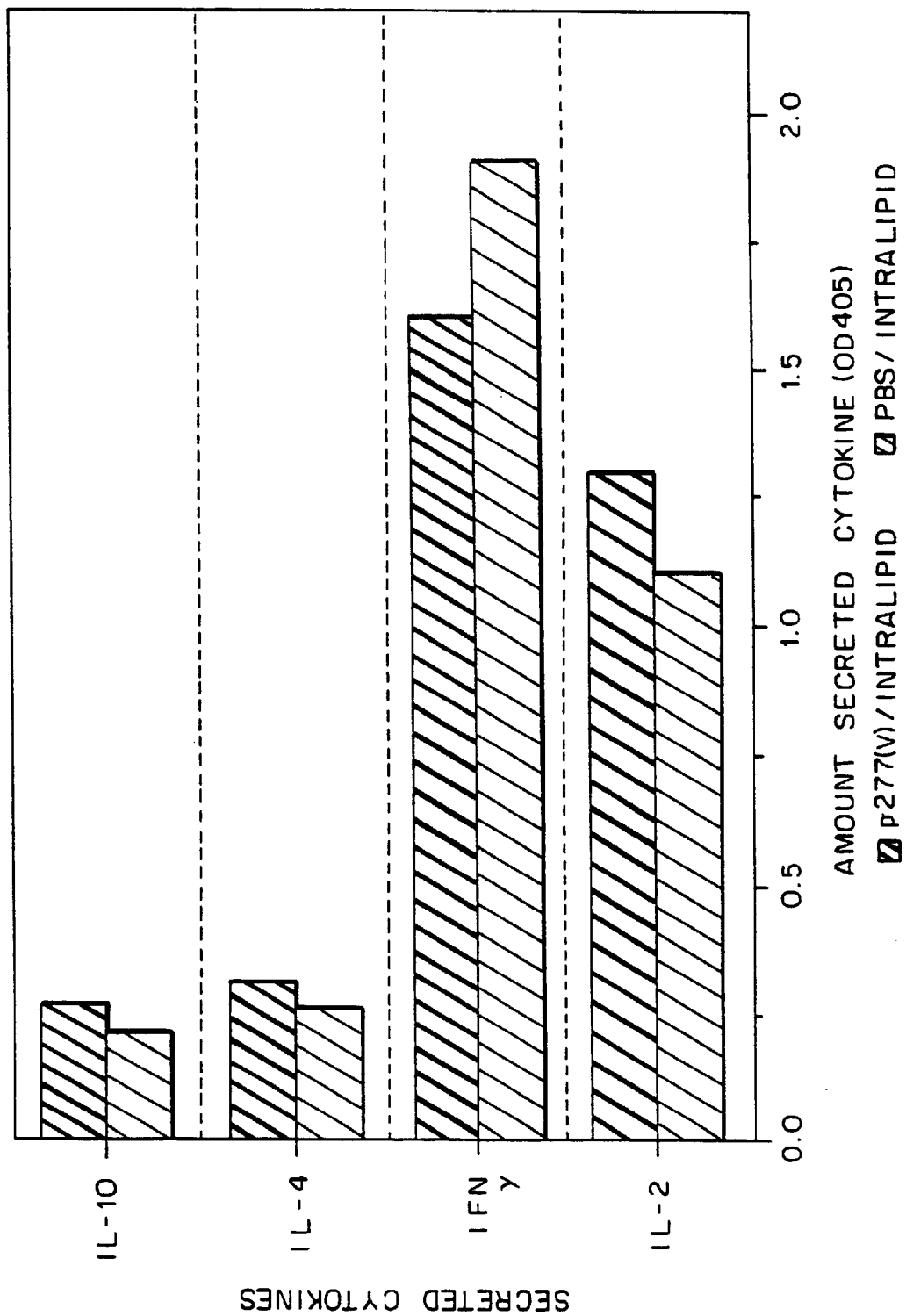

PREPARATIONS FOR THE TREATMENT OF T CELL MEDIATED DISEASES

This application is a 371 national stage application of PCT/US 96/11373, filed July 2, 1996, which claims the benefit of priority to Israel Application No. 114,458, filed July 5, 1995.

FIELD OF THE INVENTION

The present invention relates to vaccine therapy for T-cell mediated diseases, and in particular to therapeutic preparations comprising antigens recognized by T cells involved in the pathogenesis of T cell mediated diseases, such as autoimmune diseases, and a metabolizable lipid emulsion as a biologically active carrier.

BACKGROUND OF THE INVENTION

Autoimmune disorders, e.g., insulin-dependent diabetes mellitus (IDDM or type I diabetes), multiple sclerosis, rheumatoid arthritis and thyroiditis, are characterized by reactivity of the immune system to an endogenous antigen, with consequent injury to tissues. These immune responses to self-antigens are maintained by the persistent activation of self-reactive T lymphocytes.

T cells of the CD4 "helper" type have been divided into two groups by the characteristic cytokines they secrete when activated (Mosmann and Coffman, 1989). TH1 cells secrete IL-2, which induces T cell proliferation, and cytokines such as IFN-γ, which mediate tissue inflammation. TH2 cells, in contrast, secrete IL-4 and IL-10. IL-4 helps T cells secrete antibodies of certain IgG isotypes and suppresses the production of TH1 inflammatory cytokines (Banchereau et al., 1994). IL-10 indirectly inhibits TH1 activation by affecting antigen-presentation and inflammatory cytokine production by macrophages (Moore et al., 1993). It is the TH1 cells which contribute to the pathogenesis of organ-specific autoimmune diseases. TH1-type responses also appear to be involved in other T cell mediated diseases or conditions, such as contact dermatitis (Romagnani, 1994).

Peptides suitable for immunologically specific therapy of an autoimmune disease are peptides that are recognized by T cells involved in the pathogenesis of the autoimmune disease. Each autoimmune disease will have its ideal peptide for use in therapy. A disease like multiple sclerosis involving T cells reactive to self-antigens such as myelin basic protein (MBP) (Allegreta et al., 1990) will require a peptide of myelin basic protein for its therapy, as for example those described by Ota et al., 1990.

The present inventors have shown that autoimmune diseases such as type I diabetes mellitus may be treated by administering a suitable peptide in an oil vehicle. NOD mice spontaneously develop type I diabetes caused by autoimmune T cells that attack the insulin-producing β cells of the islets. The autoimmune attack is associated with T-cell reactivity to a variety of self-antigens including a peptide of the 60 kDa heat shock protein (hsp 60) and peptides of glutamic acid decarboxylase (GAD). Thus, for example, spontaneous diabetes developing in the NOD/Lt strain of mice could be treated with a peptide designated p277 corresponding to positions 437–460 of the human hsp 60 sequence (PCT Patent Publication No. WO90/10449; D. Elias and I. R. Cohen, Peptide therapy for diabetes in NOD mice, The Lancet 343:704–06, 1994); with variants of the p277 peptide in which one or both cysteine residues at positions 6 and/or 11 have been replaced by valine and/or the Thr residue at position 16 is replaced by Lys (see PCT Publication WO96/19236) and with peptides designated p12 and p32 corresponding to positions 166–185 and 466–485, respectively, of the human hsp60 sequence. See Israel Patent Application No. 114,407 of the same applicant of the present application, filed on Jun. 30, 1995. See also PCT application No. PCT/US96/11375, filed Jul. 1, 1996, claiming priority from said Israel application no. 114,407, the entire contents of which are hereby incorporated by reference.

Peptide therapy for treatment of IDDM using p12, p32, p277 or variants thereof, was found by the present inventors to be effective when the peptide was administered to mice subcutaneously (sc) in an oil vehicle such as an emulsion of mineral oil known as incomplete Freund's adjuvant (IFA). However, IFA as well as complete Freund's adjuvant (CFA; a preparation of mineral oil containing various amounts of killed organisms of Mycobacterium) are not allowed for human use because the mineral oil is not metabolizable and cannot be degraded in the body. Therefore, it would be desirable to discover an effective vehicle for peptide therapy that would be metabolizable.

Several fat emulsions have been in use for many years for intravenous nutrition of human patients. Two of the available commercial fat emulsions, known as Intralipid ("Intralipid" is a registered trade mark of Kabi Pharmacia, Sweden, for a fat emulsion for intravenous nutrition, described in U.S. Pat. No. 3,169,094) and Lipofundin (a registered trade mark of B. Braun Melsungen, Germany) contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and in Lipofundin. These fat emulsions are quite stable and have been used for intravenous nutrition of patients suffering from gastrointestinal or neurological disorders, which prevent them from receiving nutrition orally, and thus they receive the calories needed to sustain life. Usual daily doses are of up to 1 liter daily.

U.S. Pat. No. 4,073,943 issued on Feb. 14, 1978 to Wretlind et al. and U.S. Pat. No. Re. 32,393 issued on May 29, 1990 as reissue patent of U.S. Pat. No. 4,168,308 issued on Sep. 18, 1979 to Wretlind et al., describe a carrier system for use in enhancing parenteral, particularly intravenous, administration of a pharmacologically active, oil-soluble agent, comprising a stable, oil-in-water emulsion containing a pharmacologically inert lipoid as a hydrophobic phase dispersed in a hydrophilic phase, said lipid being dispersed in the emulsion as finely divided particles having a mean particle size less than 1 micron to achieve rapid onset of an acceptable therapeutic effect, said carrier system being used with an effective dose of said pharmacologically active, oil-soluble agent predominantly dissolved in said lipoid at a fraction ratio thereto in the hydrophobic phase, said therapeutic effect being attributable to said effective dose of the active agent. This carrier system is said to be suitable for administration of a water-insoluble or water-soluble, oil-soluble pharmacologically active agent that is predominantly dissolved in the lipoid phase. Examples of such pharmacologically active agents are depressants, anaesthetics, analgesics, stimulants, spasmolytics, muscle relaxants, vasodepressants and diagnostic, e.g. X-ray contrast, agents. The carrier system is said to enhance the diagnostic or therapeutic effect of the agent with a rapid onset accompanied by a reduced incidence of injury to body tissues.

Intralipid has been proposed as a non-irritating vehicle for several adjuvants for use in vaccines such as, for example, 6-O-(2-tetradecylhexadecanoyl)- and 6-O-(3-hydroxy-2-docosylhexacosanoyl)-N-acetylmuramyl-L-alanyl-D-isoglutamine (Tsujimoto et al., 1986 and 1989), avridine (Woodard and Jasman, 1985), N,N-dioctadecyl-N',N'-bis(2-hydroxyethyl) propanediamine (CP-20,961) (German Patent Application No. DE 2945788; Anderson and Reynolds, 1979; Niblack et al., 1979). Kristiansen and Sparrman, 1983, have disclosed that the immunogenicity of hemagglutinin and neuraminidase in mice is markedly increased after adsorption onto lipid particles constituting Intralipid.

None of the above publications describe the use of Intralipid as a vehicle for peptides in the treatment of autoimmune diseases, nor has there been any disclosure that Intralipid could mediate a shift of the immune response from a TH1-type response to a TH2-type response.

SUMMARY OF THE INVENTION

It has now been found, in accordance with the present invention, that metabolizable lipid emulsions, such as Intralipid and Lipofundin, can act as vehicles for peptide therapy of autoimmune diseases and of other TH1 T cell mediated diseases or conditions. It has been further found that this activity is associated with a TH1 to TH2 cytokine shift.

The present invention thus relates to a therapeutic preparation for the treatment of an autoimmune disease or other T cell mediated disease or condition, comprising a peptide or other antigen and a biologically active lipid carrier, wherein the peptide or other antigen is one recognized by inflammatory T-cells associated with the pathogenesis of said disease or condition, and wherein the biologically active lipid carrier is a fat emulsion comprising 10–20% triglycerides of plant and/or animal origin, 1.2–2.4% phospholipids of plant and/or animal origin, 2.25–4.5% osmo-regulator, 0–0.05% anti-oxidant, and sterile water to 100%.

The triglycerides and phospholipids of plant or animal origin may derive from any suitable vegetable oil, such as soybean oil, cottonseed oil, coconut oil or olive oil, or from egg-yolk or bovine serum. Preferably, the triglycerides are derived from soybean oil and the phospholipids are derived from soybean or from egg-yolk. Preferably, the triglycerides/phospholipids weight ratio is about 8:1.

Any suitable osmo-regulator may be added to the fat emulsion, preferably glycerol, xylitol or sorbitol. The fat emulsion may optionally comprise an anti-oxidant, for example 0.05% tocopherol.

In one embodiment of the invention, the fat emulsion as defined above is processed by centrifugation, e.g. at 10,000 g or higher, thus forming a small triglyceride-rich (about 90% triglycerides) layer on the top of a phospholipid-enriched aqueous dispersion containing about 1:1 triglycerides:phospholipids, and this latter aqueous dispersion is used as the lipid vehicle in the preparations of the invention.

In one preferred embodiment of the invention, the preparation is for the treatment of insulin-dependent diabetes mellitus (IDDM) and comprises a peptide derived from the human heat shock protein 60 (hsp60) that is recognized by inflammatory T-cells associated with the pathogenesis of IDDM, wherein said peptide is selected from the group of peptides appearing in the following Table 1:

TABLE 1

| Peptides | Sequence ID No: | Amino acid sequence (one letter code) |
| --- | --- | --- |
| p3 | 1 (31–50) | KFGADARALMLQGVDLLADA |
| p10 | 1 (136–155) | NPVEIRRGVMLAVDAVIAEL |
| p11 | 1 (151–170) | VIAELKKQSKPVTTPEEIAQ |
| p12 | 1 (166–185) | EEIAQVATISANGDKEIGNI |
| P14 | 1 (195–214) | RKGVITVKDGKTLNDELEII |
| p18 | 1 (255–274) | QSIVPALEIANAHRKPLVIIA |
| p20 | 1 (286–305) | LVLNRLKVGLQVVAVKAPGF |
| p24 | 1 (346–365) | GEVIVTKDDAMLLKGKGDKA |
| p29 | 1 (421–440) | VTDALNATRAAVEEGIVLGG |
| p30 | 1 (436–455) | IVLGGGCALLRCIPALDSLT |
| p32 | 1 (466–485) | EIIKRTLKIPAMTIAXNAGV |
| p35 | 1 (511–530) | VNMVEKGIIDPTKVVRTALL |
| p39 | 1 (343–366) | GKVGEVIVTKDDAM |
| p277 | 1 (437–460) | VLGGGCALLRCIPALDSLTPANED |
| p277 (Val$^6$) | *2 | VLGGGVALLRCIPALDSLTPANED |
| p277 (Val$^{11}$) | **3 | VLGGGCALLRVIPALDSLTPANED |
| p277 (Val$^6$–Val$^{11}$) | ***4 | VLGGGVALLRVIPALDSLTPANED |

*437–460 of SEQ ID NO: 1 with C-442 changed to V
**437–460 of SEQ ID NO: 1 with C-447 changed to V
***437–460 of SEQ ID NO: 1 with C-442 and C-447 changed to V The invention further relates to a method for therapy of a subject suffering from an autoimmune disease or other TH1 mediated disease or condition, which comprises administering to said subject an effective amount of a therapeutic preparation according to the invention.

BRIEF DESCRIPTION OF THE DRAWINGS

FIGS. 3A–B show that p277(Val$^6$–Val$^{11}$)/Intralipid therapy induces in NOD mice a specific switch in the profile of cytokines produced by the T-cells reactive to the p277 (Val$^6$–Val$^{11}$) peptide, as described in Example 4. FIG. 3A shows that there is a reduction of TH1 (IL-2, IFN-γ) and elevation of TH2 (IL-4, IL-10) cytokines after treatment of the mice with the p277(Val$^6$–Val$^{11}$) peptide in Intralipid and incubation of the spleen cells with p277(Val$^6$–Val$^{11}$); FIG.

3B shows that there is no change in the cytokines after treatment of the mice with the p277(Val$^6$–Val$^{11}$) peptide in Intralipid and incubation of the spleen cells with Con A.

Figure 4:
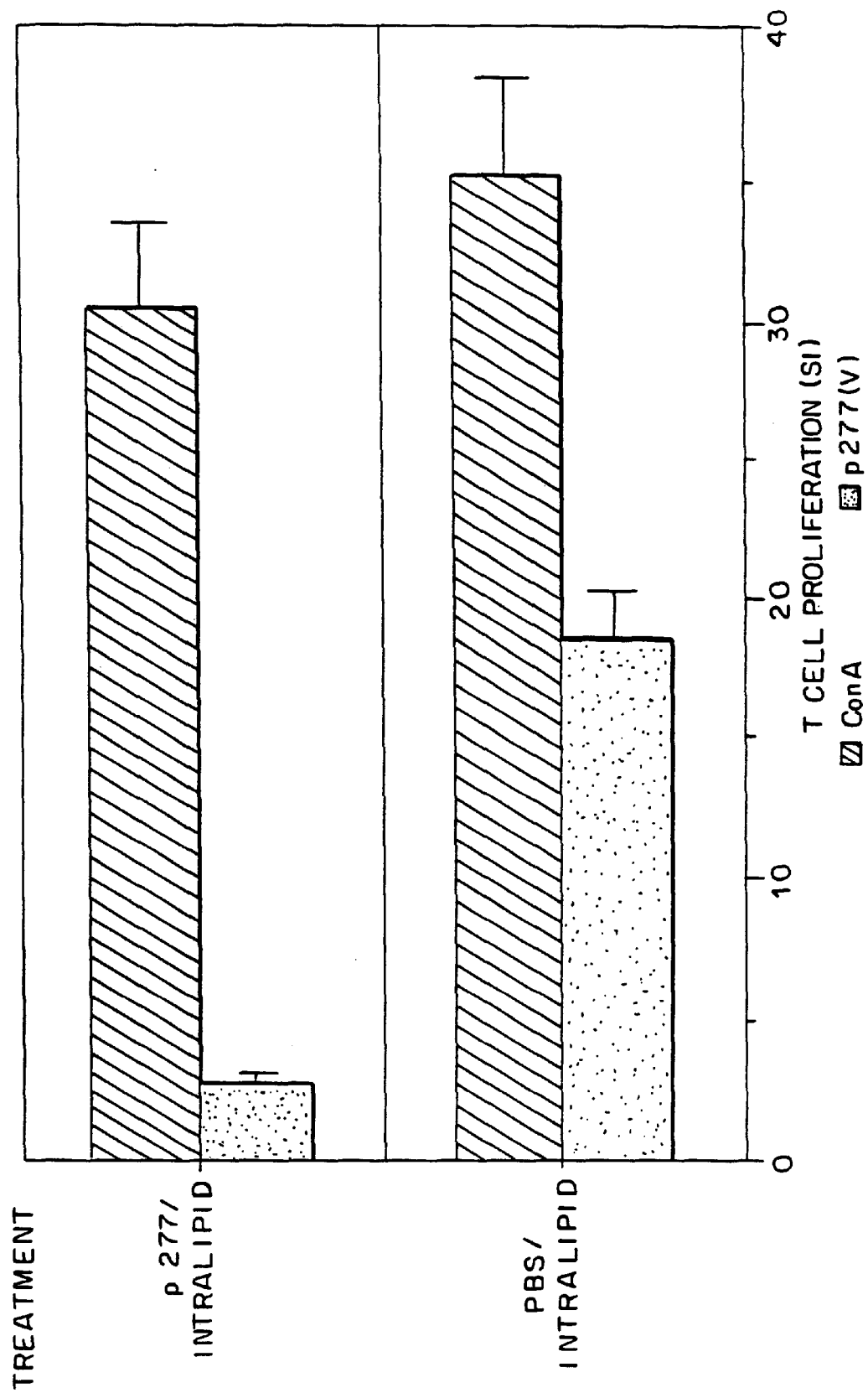

FIG. 4 shows that spontaneous T-cell proliferative responses to p277(Val$^6$–Val$^{11}$) is reduced after treatment with the p277(Val$^6$–Val$^{11}$) peptide in Intralipid, as described in Example 5.

Figure 5:
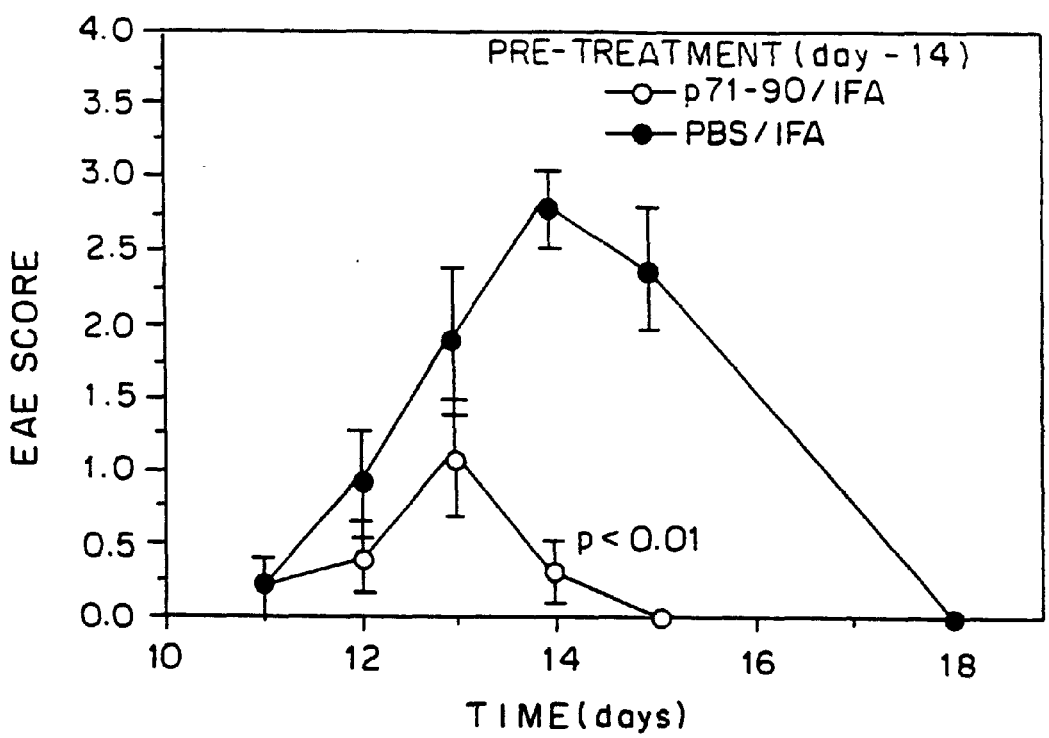

FIG. 5 shows that treatment of rats with myelin basic protein peptide p71–90 in Intralipid reduces the severity of experimental autoimmune encephalomyelitis (EAE), as described in Example 6.

Figure 6:
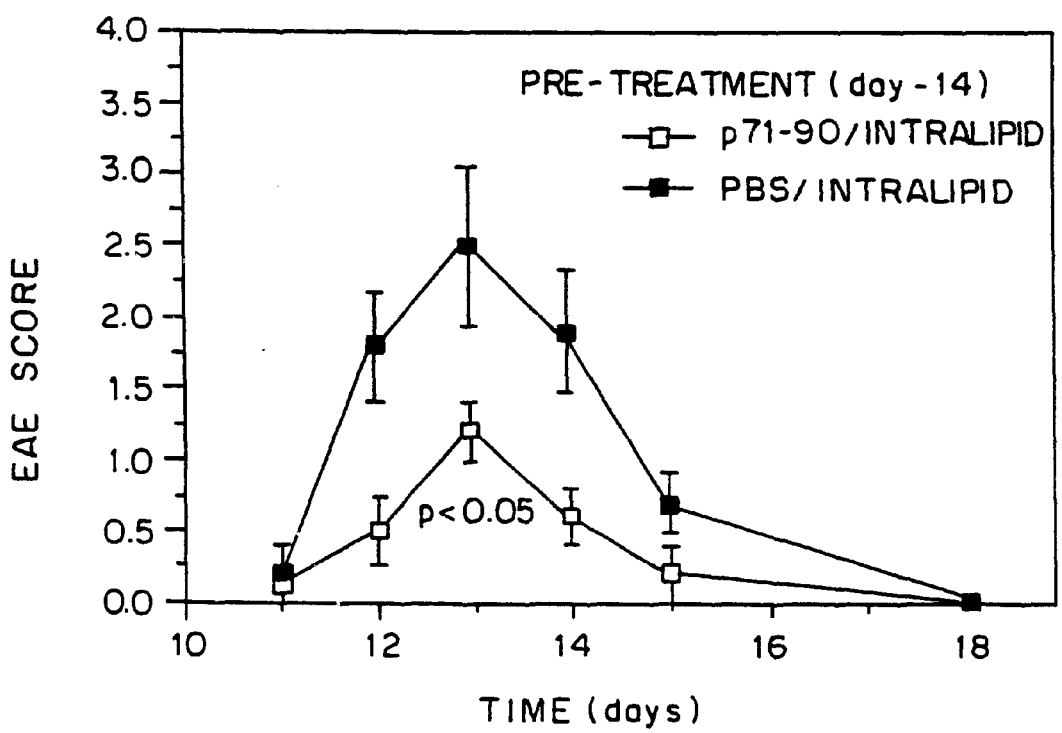

FIG. 6 shows that treatment of rats with myelin basic protein peptide p71–90 in IFA reduces the severity of experimental autoimmune encephalomyelitis (EAE), as described in Example 6.

DETAILED DESCRIPTION OF THE INVENTION

According to the present invention, it was found that p277(Val$^6$–Val$^{11}$)-peptide treatment, in an appropriate carrier, down-regulated the spontaneous T-cell proliferative responses to epitopes of both hsp60 and GAD and abolished the production of autoantibodies to hsp60, to GAD and to insulin. Arrest of the disease process was associated, not with T-cell tolerance or energy, but with a shift in the cytokines produced by the autoimmune T cells reactive to p277(Val$^6$–Val$^{11}$) from a TH1-like profile (IL-2, IFNγ) to a TH2-like profile (IL-4, IL-10). The modulation was immunologically specific; the spontaneous T-cell response of the treated mice to a bacterial hsp60 peptide remained in the TH1 mode. Thus, the diabetogenic process characterized by autoimmunity to several self antigens can be cured using one of the antigens, e.g., peptide p277(Val$^6$–Val$^{11}$).

The association of p277(Val$^6$–Val$^{11}$) therapy with a switch in reactivity to p277(Val$^6$–Val$^{11}$) from T-cell proliferation to antibodies indicates that the therapeutic effect results from a shift in the predominant cytokines produced by the autoimmune T cells in the treated mice. TH1 cells secrete IL-2, which induces T-cell proliferation, and cytokines such as IFN-γ, which mediate tissue inflammation, thereby contributing to the pathogenesis of the disease; TH2 cells, in contrast, secrete IL-4 and IL-10. IL-4 helps B cells secrete antibodies of certain IgG isotypes and suppresses the production of TH1 inflammatory cytokines. IL-10 indirectly inhibits TH1 activation by affecting antigen-presentation and inflammatory cytokine production by macrophages. Thus, TH2 cells suppress TH1 activity (see Liblau et al., 1995). The shift from TH1 to TH2-like behavior was supported by analysis of the isotypes of the antibodies produced before and after p277(Val$^6$–Val$^{11}$) therapy.

The fact that the mechanism of the therapeutic effect of the peptide in a lipid vehicle treatment is shown to involve a TH1→TH2 cytokine shift, provides the possibility of using the TH1→TH2 shift as evidence that the treatment was effective and did induce a beneficial response. In other words, the TH1→TH2 shift can serve as a surrogate marker of the response to treatment. For example, the lack of the shift can indicate a need for a second treatment. See Israel Patent Application No. 114,459 filed on Jul. 5, 1995, and the corresponding PCT application filed on even date herewith, the entire contents of which are hereby incorporated herein by reference.

The lipid emulsions of the present invention, when used as a vaccine adjuvant with the antigenic substance to which the T cells involved in the disease or condition being treated are active, serve to mediate a shift from a TH1 T cell response prior to treatment to a TH2 T cell response after treatment. This finding establishes that such lipid emulsions are tolerogenic biologically active carriers which can be used in vaccines for the treatment of any TH1 mediated disease or condition. In such vaccines, the antigen provides the immunological specificity for a therapeutic effect while the biologically active carrier of the present invention provides the biological outcome, i.e., the TH1→TH2 shift. Because of the shift mediated by said biologically active carrier of the present invention, diseases with a spectrum of autoreactivities can be turned off with a single antigen/carrier combination capable of inducing a T cell cytokine shift.

A preferred use in accordance with the present invention is in the treatment of organ-specific autoimmune diseases which are mediated by TH1 cells. Such diseases include, but are not limited to, autoimmune diseases such as IDDM, rheumatoid arthritis, multiple sclerosis and thyroiditis. The peptide used in such treatment is an autoantigen peptide. Thus, for example, for IDDM the peptide is the above-mentioned p277 peptide or the valine substituted analog p277(Val$^6$–Val$^{11}$); for multiple sclerosis such peptide is derived from myelin basic protein; for thyroiditis the peptide is thought to be derived from thyroglobulin, and for rheumatoid arthritis the autoantigen can derive from Mycobacterium organisms, e.g., *Mycobacterium tuberculosis*.

It is not critical that the antigen be a peptide. Thus, for example, TH1-mediated allergic responses which result in skin sensitivity and inflammation, such as contact dermatitis, can be treated by a vaccine containing the irritant antigen and a biologically active carrier in accordance with the present invention which will cause a shift in the cytokine response from a TH1-type to a TH2-type. Thus, while the patient will continue to have elevated antibody levels against the antigen, the inflammatory T cell response causing the skin irritation will be suppressed.

Accordingly, the tolerogenic biologically active carrier of the present invention may be used any time that it is desired to create tolerance for the antigen which the T cells are attacking, i.e., any time that a vaccine is being used to restrict a T cell mediated condition, particularly a TH1 cell mediated condition. If it can be determined which antigen is activating the response in graft rejection or in graft-versus-host disease, then the administration of such an antigen with a carrier in accordance with the present invention would be expected to facilitate the shift of the undesirable inflammatory TH1 response to a more desirable TH2 response, regardless of the overall complexity of the number of antigens to which T cells are active in such condition.

To determine the T-cell secretion of cytokines following activation with peptides, lymphocytes from the peripheral blood of patients are tested in an in vitro activation assay. Peripheral blood lymphocytes are isolated from whole heparinized blood on ficol-hypaque, and cultured with the test peptide(s) at concentrations of 5–50 μg/ml. The supernatants from the cultured T-cells are collected at different time points and tested for activity of various cytokines, by ELISA or bioassay(s).

Examples of fat emulsions that can be used in the preparations of the present invention include, but are not limited to, the commercially available Intralipid and Lipofundin for intravenous nutrition, and the fat emulsions described in the above-mentioned U.S. Pat. Nos. 3,169,096, 4,073,943 and 4,168,308, herein incorporated by reference in their entirety. However, the finding according to the present invention that these metabolizable lipids, administered previously for intravenous nutrition, may be used effectively as vehicles for therapy of T cell mediated diseases, is completely unexpected. Similarly, the discovery that these preparations are tolerogenic biologically active carriers which mediate a TH1→TH2 shift is also totally unexpected.

The fat emulsions of the present invention are preferably used as freshly prepared or after storage in a container which is not open to the atmospheric air. Prolonged storage of Intralipid, for example, while exposed to atmospheric air, causes a decrease in the pH and a corresponding decrease in the biological activity.

In one embodiment, the biologically active carrier of the invention is a fat emulsion comprising 10% soybean oil, 1.2% egg-yolk phospholipids, 2.5% glycerol and sterile water to complete 100 ml (Intralipid 10%). In another embodiment, the vehicle is a fat emulsion comprising 20% soybean oil, 2.4% egg-yolk phospholipids, 2.5% glycerol and sterile water to complete 100 ml.

In yet another embodiment, the vehicle is a fat emulsion comprising 5% soybean oil and another 5% triglycerides from animal origin, e.g. 5% medium chain triglycerides from butter, 1.2% egg-yolk lecithin, 2.5% glycerol and distilled water to complete 100 ml (Lipofundin 10%).

In one embodiment of the invention, the vehicle is a processed lipid emulsion obtained by centrifugation, e.g. at 10,000 g or higher, of the original fat emulsion defined herein, whereby a small triglyceride-rich (about 90% triglycerides) is formed on the top of a phospholipid-enriched aqueous dispersion containing about 1:1 triglycerides:phospholipids. The two phases are separated and the phospholipid-rich aqueous dispersion is used as the vehicle.

The preparations of the invention may comprise one or more peptides. Thus, for example, for the treatment of IDDM, the preparation may comprise one or more of the peptides p12, p32, p277, p277(Val$^6$), p277(Val$^{11}$), p277 (Val$^6$–Val$^{11}$), or any of the other peptides of Table 1. In one preferred embodiment, the preparation for the treatment of IDDM comprises a peptide p277 or p277(Val$^6$–Val$^{11}$) and a fat emulsion comprising 10% soybean oil, 1.2% egg-yolk phospholipids, 2.5% glycerol and sterile water to complete 100 ml (Intralipid 10%).

The invention further relates to the use of a fat emulsion as defined herein or of a processed phospholipid-enriched aqueous dispersion prepared therefrom by centrifugation for the preparation of a therapeutic preparation comprising one or more peptides or other antigens and said fat emulsion or processed aqueous dispersion as a vehicle in the therapy of autoimmune diseases or other TH1 mediated diseases or conditions.

The invention will now be illustrated by the following non-limiting examples.

EXAMPLES

Example 1
Peptide Therapy of Type I Diabetes Using p277(Val$^6$–Val$^{11}$) in Oils The efficacy of various lipid preparations as vehicles for peptide therapy of the diabetes of NOD mice was tested. In this model, autoimmune destruction of the insulin producing β-cells in the pancreas is mediated by T-lymphocytes. An inflammatory infiltrate develops around the pancreatic islets at 5–8 weeks of age and β-cell destruction leading to insulin deficiency and overt diabetes becomes manifested at 14–20 weeks of age affecting almost 100% of female NOD mice by 35–40 weeks of age.

NOD female mice were treated with 100 µg of peptide p277(Val$^6$–Val$^{11}$) per mouse sc in 0.1 ml of: (i) Phosphate-buffered saline (PBS), or (ii) a 10% lipid emulsion composed of 10% soybean oil, 1.2% egg phospholipids and 2.25% glycerol (Intralipid, Kabi Pharmacia AB, Sweden).

The incidence of diabetes at 6 months of age and the production of anti-p277(Val$^6$–Val$^{11}$) antibodies was followed. Diabetes was diagnosed as persistent hyperglycemia, blood glucose levels over 11 mmol/L measured at least twice at weekly intervals with a Beckman Glucose Analyzer II. Successful peptide treatment was assayed by maintenance of a normal blood glucose concentration (less than 11 mmol/L), remission of the intra-islet inflammation of the pancreatic islets (insulitis) and induction of antibodies to the therapeutic peptide as an indicator of a TH2-type immune response. The results are shown in Table 2.

TABLE 2

Incidence of Diabetes at 6 months.

| Treatment (%) | Diabetes | Death (%) incidence |
|---|---|---|
| p277 (Val$^6$–Val$^{11}$)/PBS | 90 | 80 |
| p277 (Val$^6$–Val$^{11}$)/Intralipid | 45# | 20# |
| none | 100 | 90 | p < 0.01 compared to untreated NOD mice.

As can be seen from Table 2, peptide treatment administered in Intralipid was effective in reducing the incidence of diabetes and death. On the other hand, treatment administered in PBS was ineffective.

Example 2
Anti-p277(Val$^6$–Val$^{11}$) Antibody Production

The protection from diabetes by treatment with the p277 (Val$^6$–Val$^{11}$) peptide is dependent on TH2 immunological reactivity to the peptide. Therefore, antibody production was measured in the p277(Val$^6$–Val$^{11}$)-immunized mice by ELISA. Maxisorp microtiter plates (Nunc) were coated with p277(Val$^6$–Val$^{11}$) peptide, 10 µg/ml, for 18 h and non-specific binding blocked with 7% milk powder for 2 h. The mouse sera, diluted 1:50, were allowed to bind for 2 h and the specific binding was detected by adding alkaline phosphatase anti-mouse IgG (Serotec) for 2 h and p-nitrophenylphosphate substrate (Sigma) for 30 min. The color intensity was measured by an ELISA reader (Anthos) at OD=405 nm.

Figure 1:
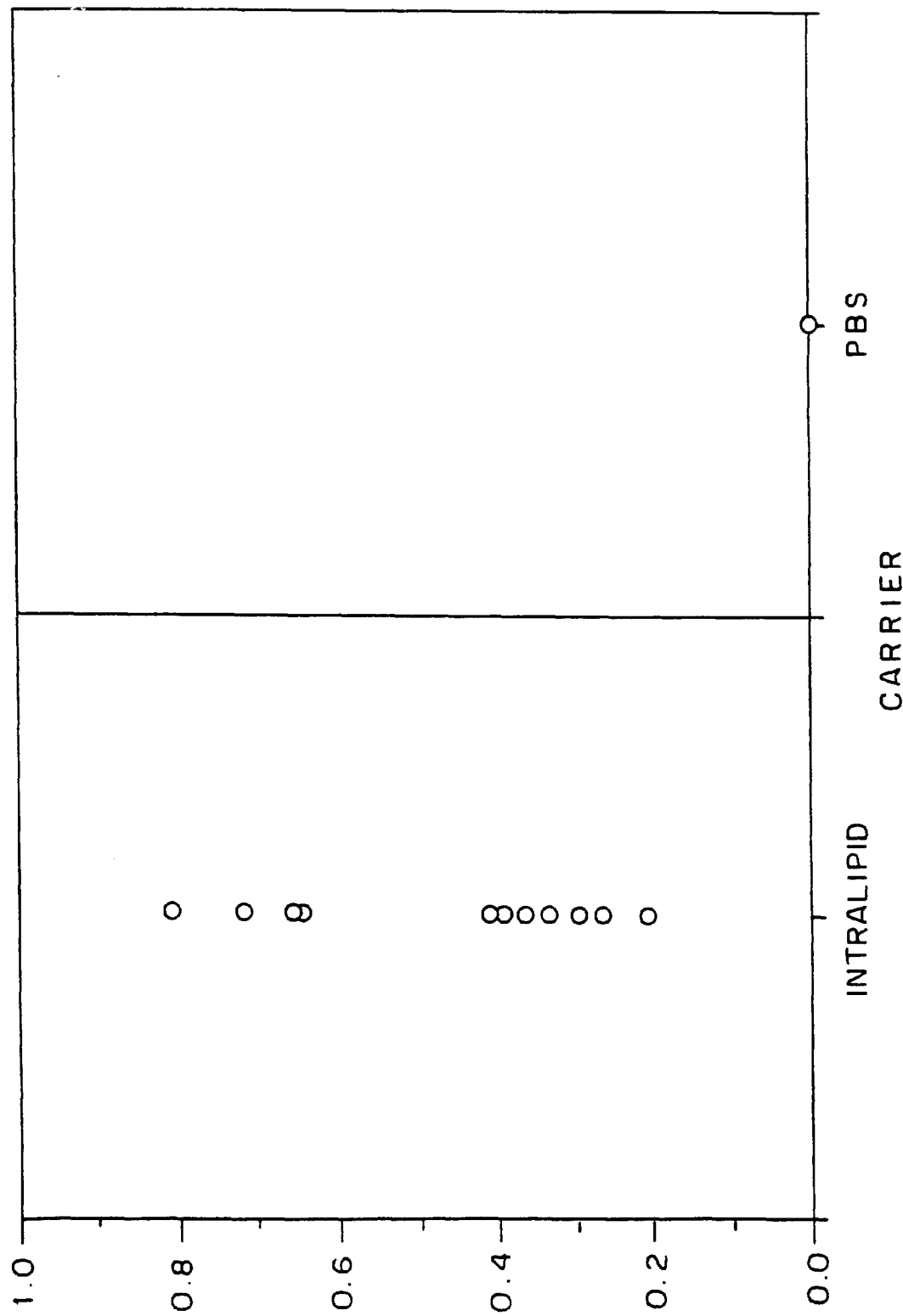
FIG. 1 shows anti-p277 antibody production in NOD mice treated with the peptide p277(Val$^6$–Val$^{11}$) in: (i) Intralipid or (ii) phosphate-buffered saline (PBS), as described in Example 2.

As can be seen from FIG. 1, NOD mice immunized to p277(Val$^6$–Val$^{11}$) in Intralipid developed peptide specific antibodies, while mice immunized to p277(Val$^6$–Val$^{11}$) in PBS showed no antibody responses at all.

Example 3
Antibody Isotypes Induced by p277(Val$^6$–Val$^{11}$) Therapy

The association of p277(Val$^6$–Val$^{11}$) Intralipid therapy with antibodies to p277(Val$^6$–Val$^{11}$) shown in Example 2, suggested that the therapeutic effect might result from a shift in the predominant cytokines produced by the autoimmune T cells. T cells of the CD4 "helper" type have been divided into two groups by the characteristic cytokines they secrete when activated (Mosmann and Coffman, 1989): TH1 cells secrete IL-2, which induces T-cell proliferation, and cytokines such as IFNγ, which mediate tissue inflammation; TH2 cells, in contrast, secrete IL-4, which "helps" B cells produce certain antibody isotypes, and IL-10 and other cytokines, which can "depress" tissue inflammation. The possibility of a shift from TH1 to TH2-like behavior was supported by analysis of the isotypes of the antibodies produced after p277(Val$^6$–Val$^{11}$) therapy.

Figure 2:
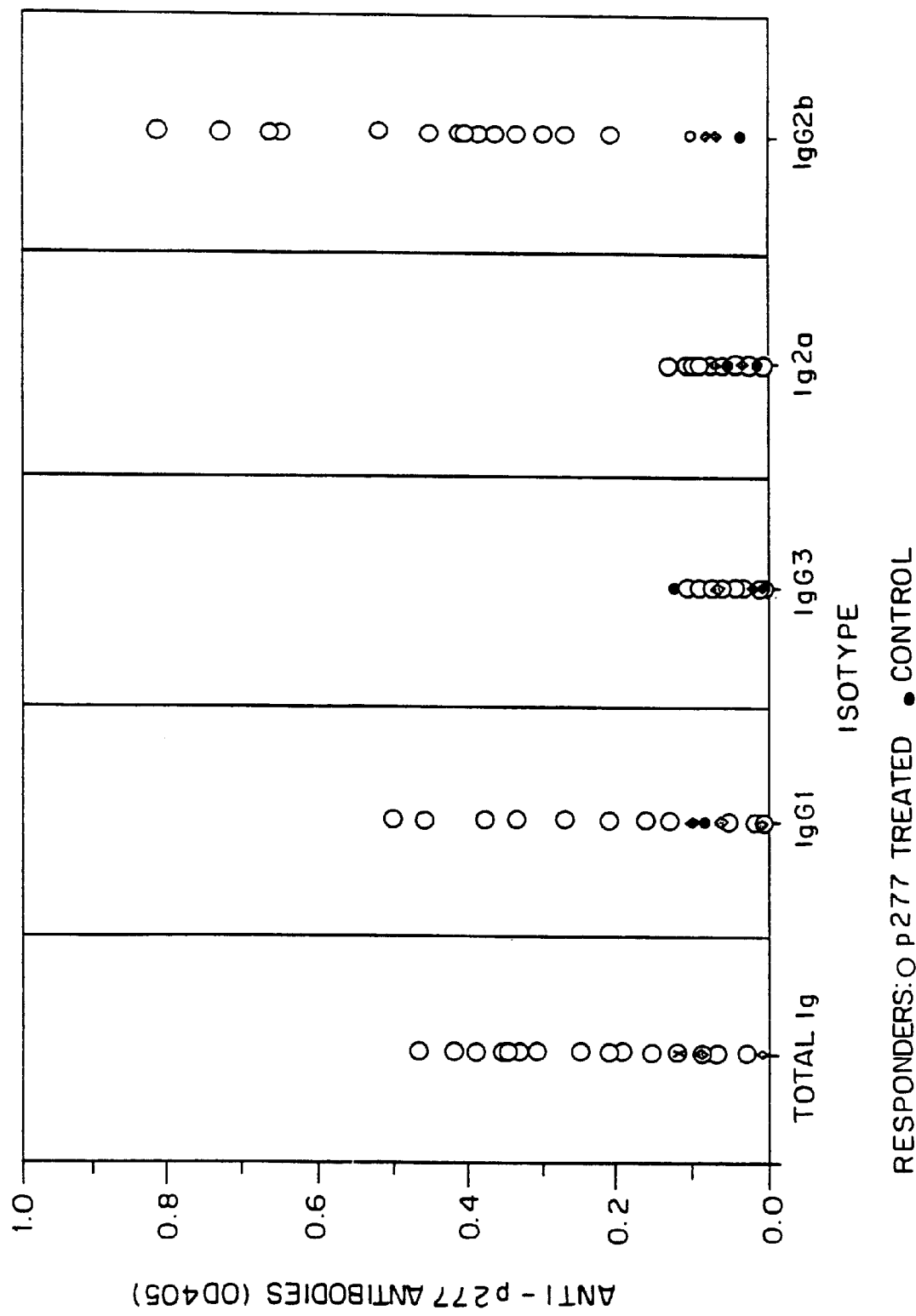
FIG. 2 shows TH2-dependent antibody isotypes induced in NOD mice by treatment with the peptide p277 (Val$^6$–Val$^{11}$) in Intralipid, as described in Example 3.

Groups of NOD mice, 3 months old, were treated with p277(Val$^6$–Val$^{11}$) or with PBS in oil as described in Example 2. The sera of individual mice were assayed for the isotypes of their antibodies to p277(Val6–Val$^{11}$) after treatment (12–15 mice per group). The antibody isotypes were detected using an ELISA assay with isotype-specific developing antibody reagents (Southern Biotechnology Associates, Birmingham, Ala.). The results are shown in FIG. 2, wherein: Antibodies to p277(Val$^6$–Val$^{11}$) in control-treated NOD mice—open circles; in p277(Val$^6$–Val$^{11}$)-treated mice—closed circles. The columns in each experiment show results from equal numbers of mice; an apparent reduction in numbers of circles is caused by superimposition.

Analysis of the antibody isotypes of the anti-p277 antibodies developing after treatment showed them to be exclusively of the IgG1 and IgG2b classes, dependent on TH2 T cells producing IL-4 (Snapper et al., 1993a) and possibly TGFβ (Snapper et al., 1993b). There were no TH1-type IgG2a antibodies induced by p277(Val$^6$–Val$^{11}$) therapy. The development of antibodies to the specific peptide used in treatment is a sign that the autoimmune T-cell responses have shifted from a damaging inflammatory mode called TH1 to a TH2 T-cell response that produces innocuous antibodies and suppresses inflammation and tissue damage (Rabinovitch, 1994).

Example 4
Peptide p277(Val$^6$–Val$^{11}$)/Intralipid Therapy Induces a Specific Switch in the Cytokine Profile To confirm the idea of a cytokine switch, the cytokines produced by the T cells reactive to the p277(Val$^6$–Val$^{11}$) in the p277(Val$^6$–Val$^{11}$)/Intralipid-treated and control mice were assayed. Concanavalin A (ConA), a T-cell mitogen, was used to activate total splenic T-cells as a control.

Groups of 10 NOD mice, 3 months old, were treated with p277(Val$^6$–Val$^{11}$) in Intralipid (closed bars) or with PBS in Intralipid (open bars; see Example 2). Five weeks later, the spleens of the mice were removed and the spleen cells were pooled. The spleen cells were incubated with Con A or p277(Val$^6$–Val$^{11}$) for 24 h (for IL-2 and IL-4 secretion) or for 48 h (for IL-10 and IFNγ secretion). The presence of the cytokines in the culture supernatants was quantitated by ELISA, using Pharmingen paired antibodies according to the Pharmingen cytokine ELISA protocol. Pharmingen recombinant mouse cytokines were used as standards for calibration curves. Briefly, flat-bottom 96-well microtiter plates were coated with rat anti-mouse cytokine mAbs for 18 h at 4° C., and the culture supernatants or recombinant mouse cytokines were added for 18 h at 4° C. The plates were washed, and biotinylated rat anti-mouse cytokine mAbs were added for 45 min at room temperature, then extensively washed, and avidin-alkaline phosphatase was added. The plates were washed, a chromogen substrate (p-nitrophenylphosphate) was added and samples were read at 405 nm in an ELISA reader. The results are shown in FIG. 3. The concentrations of cytokines are shown as the OD readings. *P<0.01.

FIG. 3A shows that the spleen cells of control mice secreted both IL-2 and IFNγ upon incubation with p277 (Val$^6$–Val$^{11}$). In contrast, the p277(Val$^6$–Val$^{11}$)-treated mice produced significantly less (P<0.01) IL-2 and IFNγ in response to incubation with peptide p277(Val$^6$–Val$^{11}$). This reduction in TH1 cytokines was specific; the p277 (Val$^6$–Val$^{11}$)-treated mice maintained their IL-2 and IFNγ cytokine responses to ConA (FIG. 3B). FIGS. 3A and 3B show the amounts of IL-10 and IL-4 produced by the spleen cells of the mice. The control mice produced very little IL-4 or IL-10 in response to p277(Val$^6$–Val$^{11}$) or Con A. In contrast, there was a significant increase in IL-10 and IL-4 in response only to p277(Val$^6$–Val$^{11}$) and only in the p277 (Val$^6$–Val$^{11}$)/Intralipid-treated mice (P<0.01). A decrease in IL-2 and IFNγ coupled with an increase in IL-10 and IL-4 confirms the shift from TH1-like behavior to TH2-like behavior. Such a shift might help explain both a decline in T-cell proliferation to p277 shown previously by the inventors (Elias et al., 1991) and the appearance of IgG1 and IgG2b antibodies to p277(Val$^6$–Val$^{11}$) according to the present invention.

Example 5
Spontaneous T-Cell Proliferative Responses to p277 (Val$^6$–Val$^{11}$) is Reduced by p277(Val$^6$–Val$^{11}$) Therapy Groups of 5 female mice of the NOD/Lt strain were treated at the age of 3 months with 100 μg of peptide p277(Val$^6$–Val$^{11}$) in Intralipid or with PBS mixed with Intralipid, sc in the back. Five weeks later, the spleens of the mice were removed and the T-cell proliferative responses were assayed in vitro to the T-cell mitogen Con A (1.25 μg/ml) or to p277(Val$^6$–Val$^{11}$) (10 μg/ml) using a standard assay. The results are shown in FIG. 4, wherein: Con A-black striped bars; p277(Val$^6$–Val$^{11}$)—grey bars. The T-cell responses were detected by the incorporation of [$^3$H] thymidine added to the wells in quadruplicate cultures for the last 18 hours of a 3-day culture. The stimulation index (SI) was computed as the ratio of the mean cpm of test cultures to the mean cpm of antigen-containing wells to control wells cultured without antigens or Con A. The standard deviations from the mean cpm were always less than 10%.

As shown in FIG. 4, the control mice tested with PBS/Intralipid showed T-cell proliferative responses to both p277(Val$^6$–Val$^{11}$) and to the T-cell mitogen Con A. In contrast, the mice treated with p277(Val$^6$–Val$^{11}$) in Intralipid showed a decrease in T-cell proliferative reactivity to p277 (Val$^6$–Val$^{11}$) but no decrease to Con A. Thus the beneficial effect of p277(Val$^6$–Val$^{11}$) peptide therapy is caused not by inactivating the autoimmune response, but by activating the autoimmunity into a different cytokine mode of behavior (Cohen, 1995). Regulation of destructive autoimmunity is programmed within the immune system (Cohen, 1992); it need only be activated by a suitable signal which requires the peptide together with the lipid vehicle; neither the peptide alone or the lipid without the peptide are effective, as shown in Table 1. These results indicate that metabolizable lipid emulsions may be use defectively as vehicles for therapy of autoimmune diseases. Each disease will require its own specific peptide, but the metabolizable lipid emulsion can be used for the various therapies.

Example 6
Administration of Peptide in Intralipid Affects Development of Experimental Autoimmune Encephalomyelitis Experimental autoimmune encephalomyelitis (EAE) is an experimental autoimmune disease of animals that is thought to model aspects of multiple sclerosis (Zamvil and Steinman, 1990). EAE can be induced in susceptible strains of rats, such as the Lewis rat, by immunization to myelin basic protein (MBP) in complete Freund's adjuvant (CFA), an emulsion of mineral oil containing killed Mycobacteria. The disease develops about 12 days after immunization and is characterized by paralysis of various degrees due to inflammation of the central nervous system. The paralysis can last up to 6 or 7 days and the rats usually recover unless they die during the peak of their acute paralysis. EAE is caused by T cells that recognize defined determinants of the MBP molecule. The major MBP determinant in the Lewis rat is composed of the peptide sequence 71–90 (Zamvil and Steinman, 1990).

We therefore performed an experiment to test whether administration of the encephalitogenic MBP peptide p71–90 in IFA could also inhibit the development of EAE. FIG. 5 shows that the administration of p71–90 in IFA 14 days before the induction of EAE led to a significant decrease in the maximal degree of paralysis compared to the control treatment with PBS emulsified in IFA, which had no effect on the severity of the disease. Thus, p71–90 given in IFA affects EAE.

However, IFA cannot be administered, as stated above, to humans because it is not metabolizable in the body and causes local inflammation. We therefore treated Lewis rats with p71–90 in Intralipid. FIG. 6 shows the results. The rats that had received p71–90 in Intralipid developed significantly less paralysis than did the control rats treated with PBS/Intralipid. Therefore, it can be concluded that a relevant peptide such as p71–90 administered in Intralipid is capable of modulating EAE in rats. Hence, the effects of peptide/Intralipid treatment are not limited to only one peptide, in one species, or to only one autoimmune disease.

Example 7

Effectiveness of New vs. Aged 10% Intralipid Emulsion

10% Intralipid emulsion was used to treat 12 week old NOD female mice with p277($Val^6$–$Val^{11}$). The emulsion was used either on the day the sealed bottle was opened, or 4 months later, after exposure to atmospheric air. The pH of the emulsion was tested at the time of preparing the peptide+emulsion for treatment. Aging was marked by a fall in pH from 8.2 to 6.7. In each experiment 10 mice were treated with the peptide+emulsion preparation, 10 mice received the emulsion alone, and 10 mice were untreated. The results are shown in Table 3.

TABLE 3

| Group | Treatment | Emulsion pH | Diabetes (%) | Mortality (%) |
|---|---|---|---|---|
| 1 | peptide + emulsion | 8.2 | 20* | 10* |
| 2 | emulsion | " | 90 | 70 |
| 3 | peptide + emulsion | 6.7 | 60 | 40 |
| 4 | emulsion | " | 80 | 60 |
| 5 | untreated | — | 90 | 80 |

*$p < 0.01$

It can be seen that the placebo-treated mice (emulsion only, groups 2 and 4) and the untreated mice (group 5) developed a similar incidence of diabetes, 80–90% at 6 months of age. In contrast, treating the mice with peptide in the newly opened emulsion protected 80% of the mice from diabetes. However, using the "aged" emulsion only protected 40%. Therefore, the emulsion was chemically unstable after exposure to air, as shown by the marked decrease in pH value. This change is relevant to its biological activity. Hence, the Intralipid is a biologically active carrier whose functional properties depend on the pH and not only on the presence of inert lipid.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present application. Therefore, such adaptations and modifications are intended to be within the meaning and range of equivalents of the disclosed embodiments, based on the teaching and guidance presented herein. It is to be understood that the phraseology of the present specification is to be interpreted by the skilled artisan in light of the teachings and guidance presented herein, in combination with the knowledge of one of ordinary skill in the art.

What is claimed is:

1. A composition consisting essentially of an antigen and a carrier, wherein the antigen is recognized by inflammatory T cells associated with the pathogenesis if diabetes and is peptide p277 (residues 437–460 of SEQ ID NO:1) or peptide p277 (Val$^6$–Val$^{11}$) (SEQ ID NO:4), and wherein the carrier induces a TH1→TH2 shift in the cytokines produced by said T cells and is a fat emulsion consisting essentially of 10–20 % triglycerides of plant and/or animal origin, 1.2–2.4% phospholipids of plant and/or animal origin, 2.25–4.5% osmoregulator, 0–0.05% antioxidant, and sterile water.

2. The composition according to claim 1, wherein the triglycerides are of plant origin.

3. The composition according to claim 2, wherein the triglyceride is derived from soybean, corronseed, coconut, or olive plants.

4. The composition according to claim 1, wherein the phospholipids are of animal origin.

5. The composition according to claim 4, wherein the phosolipids are derived from egg yolk or bovine serum.

6. The composition according to claim 1, wherein the osmo-regulator is glycerol, sorbitol or xylitol.

7. The composition according to claim 1, wherein the flat emulsion comprises 10% soybean oil, 1.2% egg-yolk phospholipids, 2.5% glycerol and sterile water.

* * * * *

UNITED STATES PATENT AND TRADEMARK OFFICE
CERTIFICATE OF CORRECTION

PATENT NO.   : 6,488,933 B2
DATED        : December 3, 2002
INVENTOR(S)  : Cohen et al.

It is certified that error appears in the above-identified patent and that said Letters Patent is hereby corrected as shown below:

Title page,
Item [57], ABSTRACT,
Last line, after "for the therapeutic treatment of such" insert -- a condition. --.

Column 17,
Line 20, change "pathogenesis if diabetes" to -- pathogenesis of diabetes --.

Column 18,
Line 18, change "corronseed," to -- cottonseed, --.
Line 23, change "phosolipids" to -- phospholipids --.
Line 26, change "flat" to -- fat --.

Signed and Sealed this

Twenty-fifth Day of February, 2003

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 573 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO: 1:

```
Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
                35                  40                  45

Asp Ala Val Ala Val Thr Met Gly Pro Lys Gly Arg Thr Val Ile Ile
            50                  55                  60

Glu Gln Gly Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
                100                 105                 110

Thr Thr Thr Ala Thr Val Leu Ala Arg Ser Ile Ala Lys Glu Gly Phe
            115                 120                 125

Glu Lys Ile Ser Lys Gly Ala Asn Pro Val Glu Ile Arg Arg Gly Val
130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
                180                 185                 190

Val Gly Arg Lys Gly Val Ile Thr Val Lys Asp Gly Lys Thr Leu Asn
                195                 200                 205

Asp Glu Leu Glu Ile Ile Glu Gly Met Lys Phe Asp Arg Gly Tyr Ile
                210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
                260                 265                 270

Ile Ile Ala Glu Asp Val Asp Gly Glu Ala Leu Ser Thr Leu Val Leu
                275                 280                 285

Asn Arg Leu Lys Val Gly Leu Gln Val Val Ala Val Lys Ala Pro Gly
290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
                340                 345                 350

Asp Asp Ala Met Leu Leu Lys Gly Lys Gly Asp Lys Ala Gln Ile Glu
                355                 360                 365

Lys Arg Ile Gln Glu Ile Ile Glu Gln Leu Asp Val Thr Thr Ser Glu
370                 375                 380
```

```
Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Cys Ala Leu Leu Arg Cys Ile
            435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
                565                 570

(2) INFORMATION FOR SEQ ID NO: 2:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Val Leu Gly Gly Gly Val Ala Leu Leu Arg Cys Ile Pro Ala Leu Asp
1               5                   10                  15

Ser Leu Thr Pro Ala Asn Glu Asp
                20

(2) INFORMATION FOR SEQ ID NO: 3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Val Leu Gly Gly Gly Cys Ala Leu Leu Arg Val Ile Pro Ala Leu Asp
1               5                   10                  15

Ser Leu Thr Pro Ala Asn Glu Asp
                20

(2) INFORMATION FOR SEQ ID NO: 4:

(i) SEQUENCE CHARACTERISTICS:
```

(A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Val Leu Gly Gly Gly Val Ala Leu Leu Arg Val Ile Pro Ala Leu Asp
1               5                   10                  15

Ser Leu Thr Pro Ala Asn Glu Asp
            20